United States Patent [19]

Pernick

[11] Patent Number: 4,465,371
[45] Date of Patent: * Aug. 14, 1984

[54] OPTICAL FLAW DETECTION METHOD AND APPARATUS

[75] Inventor: Benjamin J. Pernick, Hampton Bays, N.Y.

[73] Assignee: Grumman Aerospace Corporation, Bethpage, N.Y.

[*] Notice: The portion of the term of this patent subsequent to Jun. 15, 1999 has been disclaimed.

[21] Appl. No.: 347,075

[22] Filed: Feb. 8, 1982

Related U.S. Application Data

[63] Continuation of Ser. No. 63,729, Aug. 6, 1979, abandoned.

[51] Int. Cl.$^3$ .................... G01N 21/00; G01N 21/55
[52] U.S. Cl. ............................ 356/237; 350/162.11; 356/445
[58] Field of Search ............... 356/237, 445, 376, 355, 356/357, 359, 446; 350/162.11

[56] References Cited

U.S. PATENT DOCUMENTS

| | | | |
|---|---|---|---|
| 3,551,061 | 12/1970 | Glowa | 356/241 |
| 3,782,827 | 1/1974 | Nisenson et al. | 356/237 X |
| 3,790,287 | 2/1974 | Cuthbert et al. | 356/237 X |
| 3,804,521 | 4/1974 | Sprague | 356/359 |
| 3,857,637 | 12/1974 | Obenreder | 356/237 X |
| 3,877,777 | 4/1975 | Glenn, Jr. | 350/285 X |
| 3,879,131 | 4/1975 | Cuthbert et al. | 356/237 X |
| 3,892,492 | 7/1975 | Baker et al. | 356/237 X |
| 3,917,414 | 11/1975 | Gels et al. | 356/237 X |
| 3,922,093 | 11/1975 | Dandliker et al. | 356/237 X |
| 3,964,830 | 6/1976 | Ikeda et al. | 356/237 X |
| 3,972,616 | 8/1976 | Minami et al. | 356/237 X |
| 4,030,830 | 6/1977 | Holly | 356/237 X |
| 4,148,587 | 4/1979 | Erdmann et al. | 356/359 |
| 4,334,780 | 6/1982 | Pernick | 356/359 |

OTHER PUBLICATIONS

"Scanner for Opaque Samples", Hayes, *IBM Tech. Disclosure Bulletin*, vol. 16, #9, 2826–2828, 1974.
"Method of Checking Wall Imperfections," Heinz, Western Elec. Tech. Digest, #19, 31–32, 1970.
"Noncontact Optical Profilometer", Whitefield, Applied Optics, vol. 14, No. 10, Oct. 1975, pp. 2480–2485.

*Primary Examiner*—Bruce Y. Arnold
*Attorney, Agent, or Firm*—Morgan, Finnegan, Pine, Foley & Lee

[57] ABSTRACT

An optical method and apparatus for nondestructively inspecting a specimen for evidence of surface flaws, for example, cracks granularity and/or roughness characteristics, which would be indicative of component expected lifetime before failure are disclosed.

The distribution pattern of coherent light scattered by a surface illuminated sample is obtained with a transform lens (for a two-dimensional pattern) or a transform-cylinder lens pair (for a one-dimensional pattern). The surface scattered light distribution is inherently different for flawed and unflawed samples. Spatial frequency signatures obtained from measurements of the scattered light diffraction patterns are used to distinguish flawed from unflawed specimens. Measurements are not restricted to planar surfaces; curved sample shapes can be employed with appropriate optical component adjustments.

12 Claims, 8 Drawing Figures

UNFLAWED SURFACE

CRACK-FLAWED SURFACE

OPTICAL FLAW DETECTION METHOD AND APPARATUS

This is a continuation of application Ser. No. 063,729 filed Aug. 6, 1979 now abandoned.

BACKGROUND OF THE INVENTION

This invention relates to a method and apparatus for nondestructively detecting small surface flaws in a specimen. More specifically, it relates to the application of certain phenomena and relationships of optics to the generation, detection and interpretation of scattered light diffraction patterns created by illuminating the surface of the specimen undergoing testing with coherent light.

The surface qualities of a specimen, such as cracks, granularity and roughness characteristics, would be modified due to surface and nearby subsurface flaws. As the flaw grows in size and influence on the mechanical properties of the surrounding material, these aforementioned surface features would change as well. The altered surface features in turn modify the reflected light properties. The distribution of scattered light is thus a direct consequence of the surface features and can be used to ascertain the mechanical integrity of the sample. For example, evidence of fatigue-induced surface flaws would be sought in the signature curve of the scattered light distribution pattern due to enhanced surface granularity and microcracking.

Flaw detection techniques, such as, acoustic testing, x-rays, eddy currents, microscope examination and dye penetrants are well known to those versed in the state-of-the-art. These methods have at least one of several drawbacks. They lack the required sensitivity to find small flaws; they are not capable of wide area coverage or scanning; they cannot be readily automated; they are not adaptable to rapid measurements; components must be placed in contact with the sample under test, or require critical focusing; they involve physical or chemical hazards; they cannot readily locate the flaw location; or they do not leave the sample physically intact as a result of the test procedure.

For example, one type of flaw detection technique which does not leave the sample physically intact utilizes principles of acoustic emission. In this method the measured signal depends upon the tearing sounds associated with flaw growth. That is, further stressing of the test sample is needed in order to obtain acoustic signals. However, by the time a flaw has grown sufficiently for detection, the useful life of the structure being tested may have been materially shortened. In many high reliability applications the destructive effect of flaw growth in conjunction with structural testing is clearly undesirable.

It is apparent that major limitations of the presently used methods are that they are subject to at least one of several drawbacks and limitations previously mentioned.

It is accordingly a general object of the present invention to provide a method and apparatus for nondestructively detecting small surface flaws and the effects on the surface of nearby subsurface flaws in a specimen. More specifically, it is a general object of the invention to overcome the aforementioned limitations associated with the known flaw detection techniques.

It is a particular object of the invention to provide an optical method and apparatus for nondestructively detecting small surface flaws in a specimen.

Other objects will be apparent in the following detailed description and the practice of the invention.

SUMMARY OF THE INVENTION

The foregoing and other objects and advantages which will be apparent in the following detailed description of the preferred embodiment, or in the practice of the invention, are achieved by the invention disclosed herein, which generally may be characterized as a method and apparatus for nondestructively detecting surface flaws in a specimen, the method comprising the steps of: illuminating the surface of the specimen with a source of coherent light; forming on detecting means located in the far field a joint one-dimensional image and orthogonal Fourier transform spectrum distribution of the light scattered by the surface of the specimen; and analyzing the shape of the joint one-dimensional image and orthogonal Fourier transform spectrum distribution for evidence of surface flaws; and the apparatus comprising: coherent light means for illuminating the surface of the specimen with coherent light; cylindrical-spherical lens means for forming on detecting means located in the far field a joint one-dimensional image and orthogonal Fourier transform spectrum distribution of the light scattered by the surface of the specimen; and means for analyzing the shape of the joint one-dimensional image and orthogonal Fourier transform spectrum distribution for evidence of surface flaws.

BRIEF DESCRIPTION OF THE DRAWINGS

Serving to illustrate an exemplary embodiment of the invention are the drawings of which.

DETAILED DESCRIPTION OF THE PREFERRED EMBODIMENT

The present invention is based on the unique optical Fourier transform properties of lenses in coherent (e.g., laser) light. The characteristics of the diffracted light pattern, or the Fourier transform spectrum, of coherent light reflected from the surface of a specimen under test, such as size of the light distribution, radial, angular or other type of symmetry, energy distribution and polarization depend upon the nature of the illuminated, reflecting surface. For example, the diffraction pattern for light reflected from a smooth mirror-like surface is determined by the geometry of the illumination aperture; a well-known Airy function distribution is obtained for a circular illumination aperture. As the surface roughness level increases, the reflected light diffraction pattern becomes speckled. Nevertheless, the average light distribution in the optically formed diffraction pattern is Gaussian in shape for Gaussian surface roughness qualities.

Flaws, such as, cracks and granularity will further alter the properties of the reflected light from the surface. With a reasonable size flaw, such as, a surface crack, in the illumination field of view, the features of the diffraction pattern would be different in general from that of flaw-free regions. These differences are used as an indication of a flaw within the field of view. For example, the crack would modify the surface profile in a surrounding neighborhood. The scattered light direction and distribution would be altered from that of a relatively flat surface due to the presence of localized surface curvature. As another example, the presence of a granular surface quality due to changes in the material properties influenced by incipient flaw growth would also modify the scattered light distribution in comparison with the light distribution of an unflawed sample.

Figure 1A:
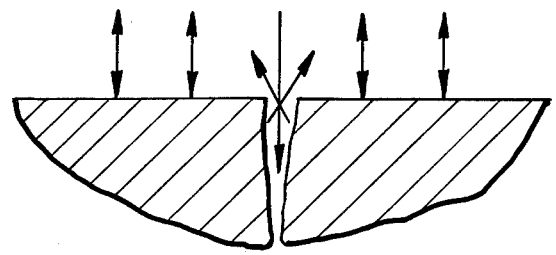
FIGS. 1a, b, c and d show several idealized surface profiles or sectional views of a surface piercing crack and diffraction pattern signatures with and without a crack in the field of view.
Figure 1B:
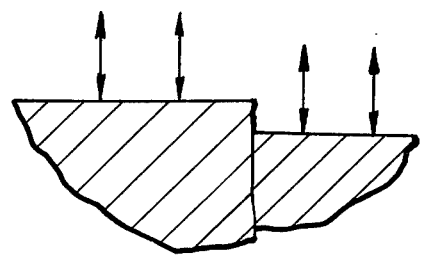
Figure 1C:
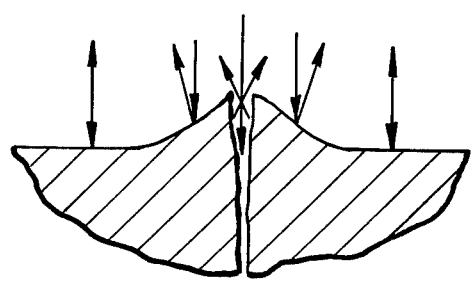
Figure 1D:
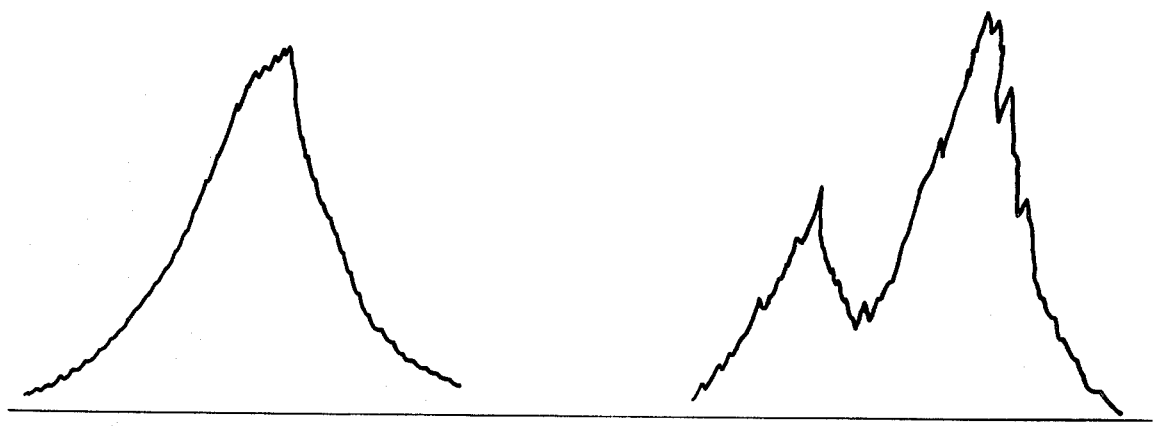

These phenomenon may be more readily understood by reference to the several surface crack models and diffraction patterns illustrated in FIGS. 1a, b, c and d. As shown in FIG. 1a, light is reflected from surface areas adjacent to the crack opening. The (idealized) diffraction pattern formed by the reflected beam components would be similar to that from an aperture with a central obscuration. The shape of the diffraction pattern signature would be different from that of an unflawed flat surface reflectance. In FIG. 1b, the diffraction pattern of the reflected beam components is modified by the optical phase difference introduced by the step change in height in the vicinity of the crack. These phase changes would modify the shape of the diffraction pattern in comparison with the pattern for an unflawed sample. In FIG. 1c, the light reflected from the sloping surfaces surrounding the crack will result in a broadening and apparent splitting of the diffraction pattern of the reflected beam due to the sloping surfaces. FIG. 1d illustrates the diffraction pattern intensity distributions (scattering angle from the surface normal) of a crack free region of a similar area with a crack in the field of view, as shown in FIG. 1c to demonstrate the apparent splitting characteristics of the diffraction pattern.

The far field diffraction pattern of light scattered by an illuminated region of a sample is obtained with a coherent optical system and is responsive to the surface quality influenced by cracks, granularity and other such flaw-induced factors. The scattered light distribution can also be anisotropic due to tooling marks, preferential wear, etc. A joint spherial-cylinder lens pairs forms a one-dimensional transform spectrum at favorable angular orientations about the optic axis with respect to the sample to circumvent these complications and provide useful spectrum averaging as well.

Figure 2:
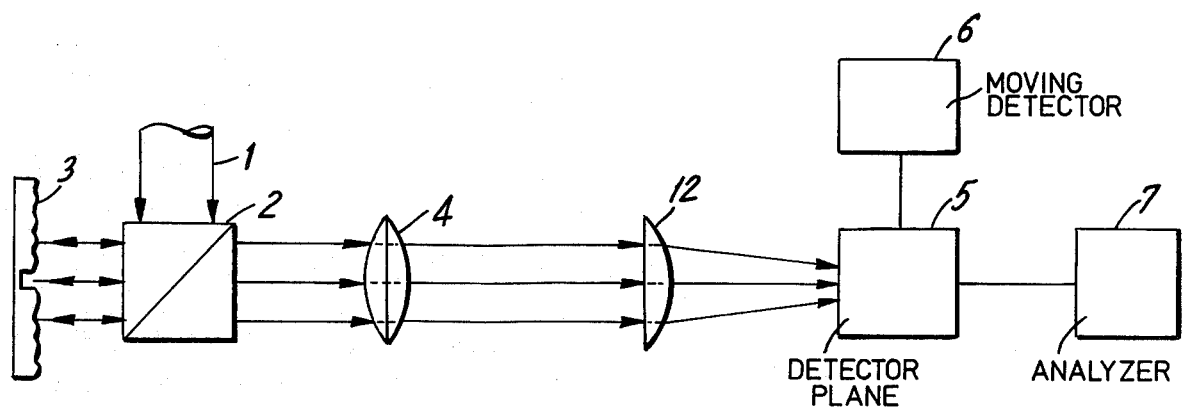
FIG. 2 is a schematic illustration of the optical flaw detection apparatus, in accordance with the present invention, with a one-dimensional reimaging capability for one-dimensional measurements.

Referring now to FIG. 2, a schematic illustration of the optical flaw detection apparatus, with a one-dimensional reimaging capability for one-dimensional spectrum measurements in accordance with the present invention, is illustrated. As shown therein, light from a coherent source 1, such as, for example, a laser, is deflected by a beam splitter 2 onto the specimen 3 undergoing inspection. The light reflected and scattered by the surface of the specimen 3 is collected with a spherical (transform) lens 4 and reimaged in one direction by a cylindrical lens 12 whose focusing action is in the plane of the figure. The cylindrical lens 12 is positioned such that a one-dimensional image of the illuminated area is formed at the detector plane 5. The detector 5 is located in or near the back focal plane of the transform lens 4 such that components of the scattered light diffraction pattern normal to the plane of the figure (and thus unaffected by the cylindrical lens), are focused onto the detector. It is noted that other lens combinations can be used to vary the size of the imagery and of the diffraction pattern by methods well known to those versed in the state-of-the-art. Similarly, it is noted that the position of the transform and cylinder lenses can be reversed to accommodate such design features as optical magnification, overall size, etc. If the diffraction pattern displayed in this plane is too small, a second lens (not shown) could be conveniently used to further enlarge the pattern. The distribution of the scattered light pattern is measured and mapped by scanning with a moving detector 6. If desired, the moving detector 6 could be replaced with a fixed detector array. The mapped distribution of the scattered light is presented to analyzer 7 for analysis and flaw signature recognition.

The light beam size used to illuminate an area of the specimen would be established by optical components and methods not shown in the figure. These components and methods are known to those experienced in the technology. Other modifications of the illustrated optical system may be apparent from the teachings of this system. For example, the beam splitting means may be eliminated and the illumination beam may be directed at an angle to the surface of the specimen.

It is noted that if a two-dimensional pattern is to be used instead of a one-dimensional pattern, the cylindrical lens 12 is removed, all other components in FIG. 2 have the same functions as previously mentioned.

Also, it is to be noted that the sample can be illuminated with diverging or converging beams, as well as a collimated beam. External means to form such beams are known to those versed in the state-of-the-art and are not shown in the figure. Other optical components of the system would be located in accord with the mode of illumination, as is well known.

The illumination field of view is defined by the laser beam diameter and can be set by well known optical methods. The beam diameter is typically of the order of millimeters to tens of millimeters. Full coverage of the surface of a large specimen to be inspected is accomplished by moving the specimen with respect to the laser beam by well known methods. The laser wavelength serves as a scaling parameter to alter the angular spread of scattered light from a rough surface and improve the system sensitivity in detecting relatively small flaws.

Figure 3:
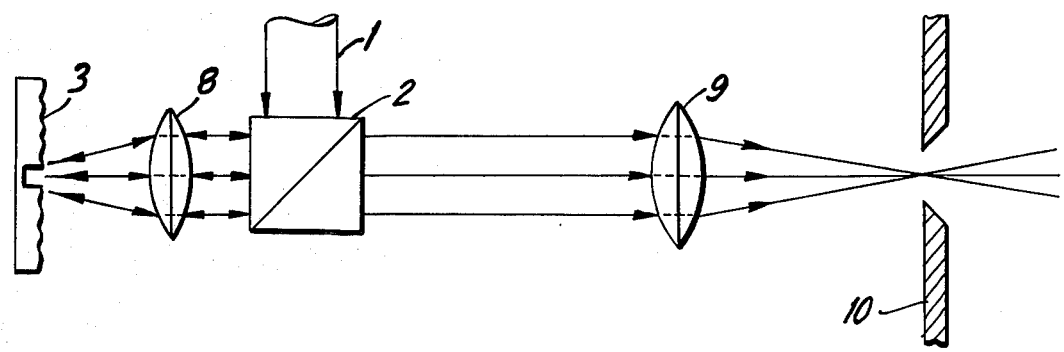
FIG. 3 illustrates the utilization of a lens system adapted to form an image prior to collecting the scattered light diffraction pattern for detecting small flaws.

Referring to FIG. 3, a means to illuminate the surface of a specimen with a lens system to form an image prior to collecting the scattered light onto the detector in order to find small flaws on the sample is illustrated. As shown therein, a coherent light beam 1 is partitioned with a beam splitter 2 as before. One portion of the light beam is focused by a lens 8 onto the surface of the specimen 3 under test. Backscattered and reflected light is also collected with the lens 8 and imaged by a second lens 9, onto an aperture 10 that defines the field of view of the final image to be processed.

Figure 4A:
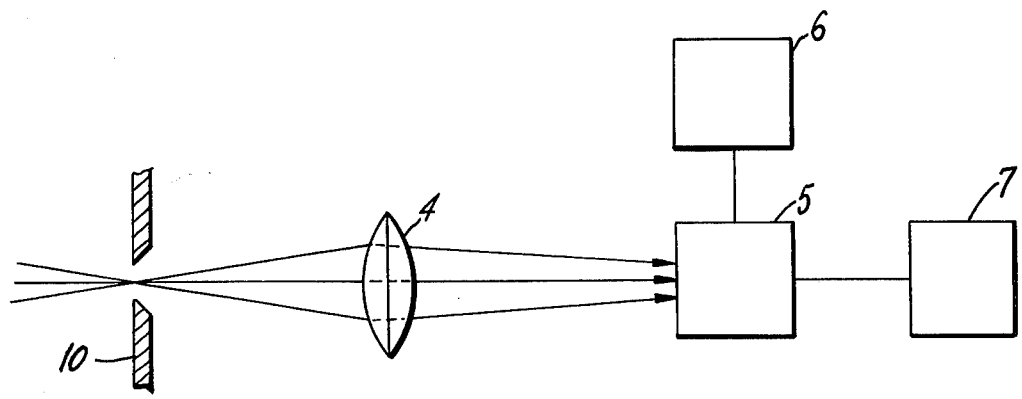
FIG. 4a is a schematic illustration of an optical system utilized to form a two-dimensional optical diffraction pattern adapted to the optical setup of FIG. 3.

The two-dimensional diffraction pattern for the image contained within the aperture 10 is obtained with the optical system schematically illustrated in FIG. 4a.

As shown therein, the light transmitted through the aperture 10 is collected with a transform lens 4 and focused onto the detector plane 5. The two-dimensional distribution of the scattered light pattern is measured and mapped by scanning with a moving detector 6. The mapped distribution of the scattered light pattern is presented to analyzer 7 for analysis and flaw signature recognition, and to a data storage facility (not shown) for archival storage and post processing.

It is known in the technology that the light distibution in the back focal plane of the transform lens 4 is related to the diffraction properties of the image contained within the aperture 10. Mathematically, the diffraction pattern distribution is related to the image distribution by a Fourier transformation. This information would help a user to interpret the diffraction pattern observed in the detector plane 5.

Figure 4B:
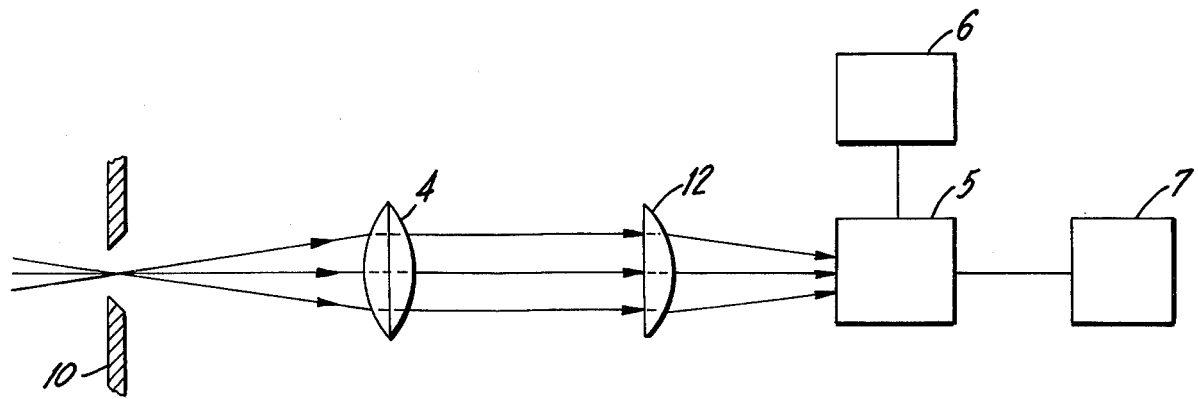
FIG. 4b is a schematic illustration of an optical system utilized to form a one-dimensional optical diffraction pattern adapted to the optical setup of FIG. 3.

The one-dimensional diffraction pattern for the image contained within the aperture 10 is obtained with the optical system schematically illustrated in FIG. 4b. As shown therein, a cylinder lens 12 with focusing properties in only one direction is used to reimage the light passing through the transform lens 4. As configured, only the diffraction pattern in the vertical direction is reimaged. The diffraction pattern in the other orthogonal direction (out of the plane of the page) is not affected by the cylinder lens. The reimaged light is focused onto the detector plane 5. The resulting one-dimensional distribution of the scattered light pattern is measured and mapped with a linear array of detectors 6. The mapped distribution of the scattered light pattern is presented to analyzer 7 for analysis and flaw signature recognition, and to a data storage facility (not shown) for archival storage and post processing.

It is to be noted that the cylinder lens can be rotated about its optic axis to be positioned in a favorable way to achieve sensitivity in a particular direction, for example, parallel to the surface crack direction.

Also, it is to be noted that these optical systems are not restricted to use with essentially flat surfaces. Curved surfaces can be utilized with appropriate modifications to the illumination optical setup and to position of optical components shown in the figures. Furthermore, it is to be noted that differences in the diffraction pattern distribution from unflawed areas due to surface flaws in the field of view are obtained with all of the above mentioned optical systems, and other setups derived from these teachings. The presence of a flaw on the sample would be evident by such diffraction pattern changes such as, for example, an apparent splitting of the distribution, a broadening of the pattern, or an alteration in the shape and/or symmetry of the content of the diffraction pattern.

It is clear that the above description of the preferred embodiment in no way limits the scope of the present invention which is defined by the following claims.

What is claimed is:

1. A method for nondestructively detecting surface flaws in a specimen comprising the steps of:
    (a) illuminating the surface of the specimen with a source of coherent light;
    (b) forming on detecting means located in the far field a joint one-dimensional image and orthogonal Fourier transform spectrum distribution of the light scattered by the surface of the specimen; and
    (c) analyzing the shape of the joint one-dimensional image and orthogonal Fourier transform spectrum distribution for evidence of surface flaws.

2. A method for nondestructively detecting surface flaws in a specimen comprising the steps of:
    (a) illuminating the surface of the specimen with a source of coherent light;
    (b) focusing in one direction on detecting means located in the far field a one-dimensional Fourier transform spectrum distribution of the light scattered by the surface of the specimen;
    (c) imaging simultaneously in an orthogonal direction on said detecting means a one-dimensional image distribution of the light scattered by the surface of the specimen;
    (d) mapping the joint one-dimensional image and orthogonal Fourier transform spectrum distribution; and
    (e) analyzing the shape of the mapped joint one-dimensional image and Fourier transform spectrum distribution for evidence of surface flaws.

3. A method as recited in claim 2 including the step of moving the specimen in a predetermined manner relative to said source of coherent light to evaluate an extended area of the surface.

4. A method as recited in claim 2 wherein the step of illuminating the surface of the specimen includes illuminating beam splitting means with a source of coherent light; and relecting one of the resulting divided beams of light at an arbitrary angle between zero and ninety degrees onto the surface of the specimen.

5. A method as recited in claim 4 further including the step of transmitting selectively through aperture means only a portion of the light scattered by the surface of the specimen.

6. Apparatus for nondestructively detecting surface flaws in a specimen comprising:
    (a) coherent light means for illuminating the surface of the specimen with coherent light;
    (b) cylindrical-spherical lens means for forming on detecting means located in the far field a joint one-dimensionald image and orthogonal Fourier transform spectrum distribution of the light scattered by the surface of the specimen; and
    (c) means for analyzing the shape of the joint one-dimensional image and orthogonal Fourier transform spectrum distribution for evidence of surface flaws.

7. Apparatus for nondestructively detecting surface flaws in a specimen comprising:
    (a) laser means for illuminating the surface of the specimen with coherent light;
    (b) spherical lens means for focusing in one direction on detecting means located in the far field a one-dimensional Fourier transform spectrum distribution of the light scattered by the surface of the specimen;
    (c) cylindrical lens means for imaging simultaneously in an orthogonal direction on said detecting means a one-dimensional image distribution of the light scattered by the surface of the specimen;
    (d) means for mapping the joint one-dimensional image and orthogonal Fourier transform spectrum distribution; and
    (e) means for analyzing the shape of the mapped joint one-dimensional image and orthogonal Fourier transform spectrum distribution for evidence of surface flaws.

8. Apparatus as recited in claim 7 including means for moving the specimen in a predetermined manner relative to said laser means to evaluate an extended area of the surface.

9. Apparatus as recited in claim 7 including beam splitting means interposed between the specimen and said laser means for reflecting a divided beam of light at an arbitrary angle between zero and ninetyy degrees onto the surface of the specimen.

10. Apparatus as recited in claim 9 further including aperture means interposed between the specimen and said cylindrical-spherical lens means for transmitting selectively only a portion of the light scattered by the surface of the specimen to said cylindrical-spherical lens means.

11. Apparatus as recited in claim 10 further including means for rotating one of said cylindrical-spherical lens means in a predetermined manner to achieve sensitivity in a particular direction.

12. Apparatus as recited in claim 11 further including means for moving the specimen in a predetermined manner relative to said laser means to evaluate an extended area of the surface.

* * * * *